US00PP28395P3

(12) United States Plant Patent
Warner

(10) Patent No.: US PP28,395 P3
(45) Date of Patent: Sep. 19, 2017

(54) SHRUB ROSE PLANT NAMED 'CHEWPATOUT'

(50) Latin Name: ***Rosa* hybrid**
Varietal Denomination: ChewPatout

(71) Applicant: Christopher Hugh Warner, Brockton (GB)

(72) Inventor: Christopher Hugh Warner, Brockton (GB)

(73) Assignee: Spring Meadow Nursery, Inc, Lerand Haven, MI (US)

( * ) Notice: Subject to any disclaimer, the term of this patent is extended or adjusted under 35 U.S.C. 154(b) by 11 days.

(21) Appl. No.: 14/757,061

(22) Filed: Nov. 12, 2015

(65) Prior Publication Data

US 2017/0142878 P1 May 18, 2017

(51) Int. Cl.
*A01H 5/02* (2006.01)

(52) U.S. Cl.
USPC ..... Plt./108

(58) Field of Classification Search
USPC ..... Plt./101, 102, 108
See application file for complete search history.

*Primary Examiner* — Susan McCormick Ewoldt
(74) *Attorney, Agent, or Firm* — Cassandra Bright

(57) ABSTRACT

A new and distinct *Rosa* hybrid named 'ChewPatout' is disclosed, characterized by semi double red to red-purple flowers. Plants are compact, resist blackspot and powdery mildew, and re-bloom easily. The new cultivar is a *Rosa* typically suited for outdoor ornamental container and landscape use.

2 Drawing Sheets

Latin name of the genus and species: *Rosa* hybrid.
Variety denomination: 'Chewpatout'.

BACKGROUND OF THE INVENTION

The new *Rosa* cultivar is a product of a planned breeding program conducted by Christopher Hugh Warner in Brockton, Newport Shromshire, United Kingdom. The objective of the propagation was to produce new *Rosa* varieties for ornamental commercial applications. The cross resulting in this new variety was made during June of 2005.

The seed parent is the unpatented, variety *Rosa* hybrid 'Pathfinder'. The pollen parent is *Rosa* hybrid 'Radrazz', U.S. Plant Pat. No. 11,836. The new variety was discovered in June of 2007 by the inventor in a group of seedlings resulting from the 2005 crossing, in a research greenhouse in Brockton, Newport Shromshire, United Kingdom.

Asexual reproduction of the new cultivar was performed by vegetative cuttings. This was first performed at a research greenhouse in Brockton, Newport Shromshire in July 2008 and has shown that the unique features of this cultivar are stable and reproduced true to type in successive generations.

SUMMARY OF THE INVENTION

The cultivar 'ChewPatout' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'ChewPatout' These characteristics in combination distinguish 'ChewPatout' as a new and distinct *Rosa* cultivar:

1. Bright red flowers
2. Good resistance to powdery mildew and blackspot of garden roses.
3. Easy repeat flowering
4. Semi-double flowers, with 15 to 19 petals per flower.

PARENTAL COMPARISON

The new variety differs from the seed parent in the following:

1. The new variety has red to red-purple colored petals; the seed parent has light pink petals.
2. The new variety has a smaller diameter flower than the seed parent.

The new variety differs from the pollen parent in the following:

1. The new variety has red to red-purple colored petals; the pollen parent has lighter pink petals.
2. The new variety has more petals per flower than the seed parent.
3.

COMMERCIAL COMPARISON

Plants of the new cultivar 'ChewPatout' are similar to the commercial variety *Rosa* hybrid 'Meiboulka' U.S. Plant Pat. No. 19,258, in most horticultural characteristics. 'However, the new variety differs from 'Meiboulka' in the following:

1. Mature upper surface petal color of 'ChewPatout' is red-purple 60A, flower color of 'Meiboulka' is red-purple 63A, with Red 53A.
2. Flowers of the new variety have approximately 15 to 19 petals, flowers of 'Meiboulka' average 5 to 7 petals.

BRIEF DESCRIPTION OF THE PHOTOGRAPHS

The accompanying color photographs illustrate the typical characteristics of the new variety 'ChewPatout'.

Figure 1:
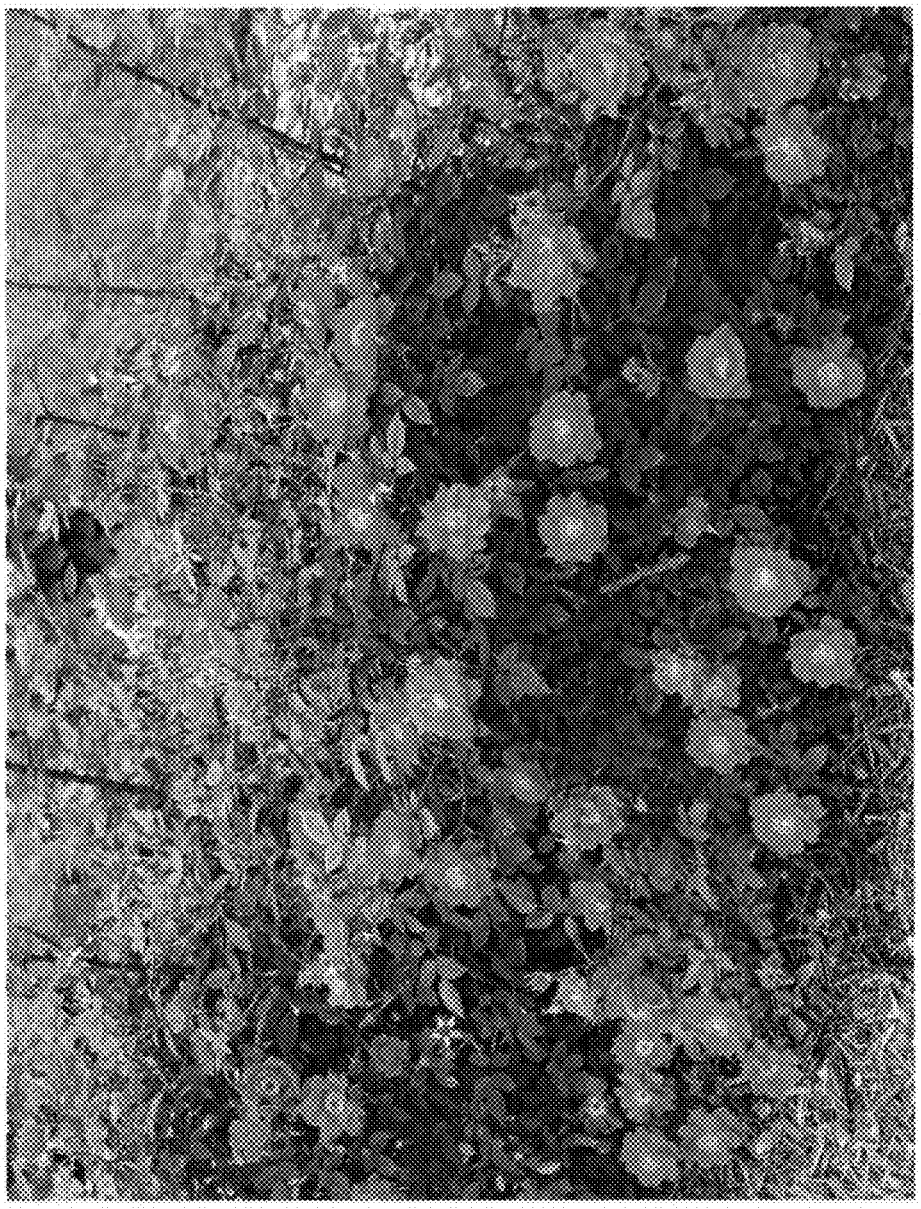
FIG. 1 Illustrates a typical plant of 'ChewPatout' grown in the ground, at approximately 2 year old.
Figure 2:
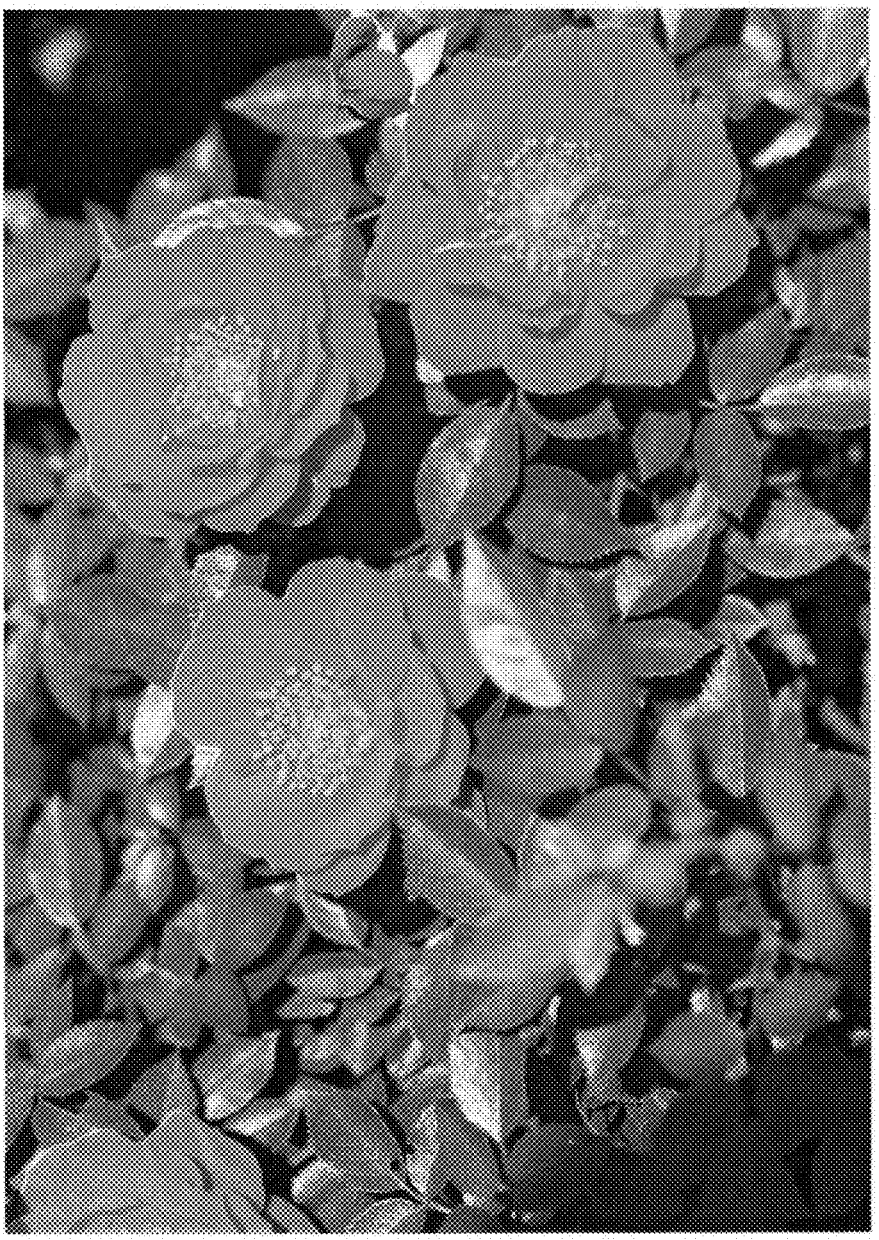
FIG. 2 illustrates a close up view of typical flowers and foliage of the new variety.

The photographs were taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Colour Chart 2007, except where general terms of ordinary dictionary significance are used. The following observations and measurements describe 'ChewPatout' plants grown in a poly house greenhouse in Grand Haven, Mich. The growing temperature ranged from 5° C. to 10° C. at night and 18° C. to 27° C. during the day. No artificial light, photoperiodic treatments or chemical treatments were given to the plants. Plants were note pinched and were grown under shade cloth. Measurements and numerical values represent averages of typical flowering types.

Botanical classification: *Rosa* hybrid 'ChewPatout'.

Age of the plant described: Approximately 2 to 3 years.

Container size of the plant described: 2 gallon.

Commercial classification: Shrub.

PROPAGATION

Typical method: Softwood cuttings.

Time to initiate rooting: Approximately 30 days in the summer at about 20° C.

Time to produce a rooted plantlet: Approximately 120 days at 20° C. or higher.

Root description: Moderately dense roots becoming slightly woody with age. Roots colored white when young, brown with age. Not accurately assigned a color with R.H.S. chart.

PLANT

Plant habit: Compact, mounding garden rose.

Height: 58 cm.

Plant spread: 50 cm.

Growth rate: Moderate.

Branching characteristics: Densely branched.

Branching characteristics:

- *Length of primary lateral branches.*—48 cm.
- *Diameter of lateral branches.*—0.6 cm.
- *Quantity of lateral branches.*—Varies, average 24.

Branching arrangement: Basal.

Thorns:

- *Number of thorns per linear centimeter.*—3-4.
- *Shape.*—Narrow deltoid, bent downward.
- *Base size.*—Average 0.7 cm.
- *Height.*—Average 0.8 cm.
- *Apex.*—Acicular.
- *Color.*—Immature: Near RHS Yellow-Green 145A on underside and near RHS Greyed-Red 181A on top of thorn. Mature: Near RHS Yellow-Green 145A on underside and near RHS Greyed-Red 181A on top of thorn.

FOLIAGE

Leaf:

- *Arrangement.*—Alternate, compound.
- *Quantity.*—About 35 per lateral branch.
- *Average length.*—About 7.5 cm.
- *Average width.*—About 4.5 cm.

Leaflet:

- *Quantity.*—5-7 per leaf.
- *Average length.*—2.5 cm.
- *Average width.*—2.0 cm.
- *Shape of blade.*—Elliptic.
- *Apex.*—Acute to apiculate.
- *Base.*—Rounded.
- *Margin.*—Serrulate.
- *Texture of top surface.*—Smooth, glossy.
- *Texture of bottom surface.*—Smooth, glossy.
- *Leaf internode length.*—3.5 cm.
- *Color.*—Young foliage upper side: Near RHS Green 139A. Young foliage under side: Near RHS Green 138A. Mature foliage upper side: Near RHS Green 139A. Mature foliage under side: Near RHS Green 138A.
- *Venation.*—Type: pinnate. Venation color upper side: Midrib near RHS Yellow-Green 145A, other veins near RHS Green 139A. Venation color under side: Midrib near RHS Yellow-Green 145B, other veins near RHS Green 138A.
- *Petiole.*—Length: 2.5 cm. Width: 0.3 cm. Color: Near RHS Yellow-Green 144B. Texture: Smooth.
- *Leaflet petiole.*—Length: 1 mm. Width: 1 mm. Color: Near RHS Yellow-Green 145A upper surface, 145B lower surface. Texture: Glabrous with micro thorns.
- *Stipule.*—Quantity: 2. Shape: Linear. Apex: Acicular. Base: Fused along petiole, base truncate. Margin: Ciliate. Length: 1.2 to 2.2 cm. Width: 2 mm. Texture: Glabrous, upper and lower surfaces. Color: Upper surface near RHS Yellow-Green 145A, lower surfaces near Yellow-Green 145B.

FLOWER

Natural flowering season: Spring through summer.

Flower arrangement: Single flowers occurring at branch terminus. 1 to 5 flowers per terminus. Flower shape is round.

Peduncle:

- *Length.*—2.5 cm.
- *Diameter.*—0.2 cm.
- *Strength.*—Strong.
- *Angle.*—Approximately 75°.
- *Texture.*—Glabrous, slightly prickly.
- *Color.*—Yellow-Green 144A.

Petals:

- *Petal arrangement.*—Semi-double whorl.
- *Size.*—Length: 2.5-3.0 cm. Width: 2.5 cm.
- *Shape.*—Obovate.
- *Margin.*—Entire.
- *Apex.*—Retuse.
- *Base.*—Acute.
- *Petal quantity.*—15-19.
- *Texture.*—Glabrous, silky.
- *Aspect.*—Weak to no undulation.

Color:

*Petals*.—When opening: Upper surface: Near RHS Red 45B; 0.45 cm diameter at base is near RHS Yellow 13B. Lower surface: Near RHS Red 53C; 0.45 cm diameter at base is near RHS Yellow-Orange 14C. Fully opened: Upper surface: Near RHS Red-Purple 60A. Lower surface: Near RHS Red-Purple 63A. Color changes when aging: Fades to near RHS Red-Purple 61A.

Bud:

*Shape*.—Ovate.

*Length*.—About 1.5 cm.

*Diameter*.—About 9.5 cm.

*Color*.—Near RHS Yellow-Green 144A.

Sepals:

*Length*.—2.2 cm.

*Width*.—0.5 cm.

*Shape*.—Acuminate.

*Color*.—Immature plant: Upper side: Near RHS Yellow-Green 145B; center near RHS Green 141A. Under side: Near RHS Green 143A. Mature Plant: Upper side: Near RHS Yellow-Green 145B; center near Green 141A. Under side: Near RHS Green 143A.

*Texture*.—Smooth/pubescent.

Fragrance: Light and sweet.

REPRODUCTIVE ORGANS

Stamens:

*Number*.—130.

*Filament length*.—About 0.8-1.0 cm.

*Filament color*.—Near RHS Yellow-Orange 17B.

*Anthers*.—Length: 0.1 cm. Shape: Club-like. Color: Near RHS Yellow-Orange 17A. Pollen: Quantity: Moderate. Color: Near RHS Yellow-Orange 17A.

Pistil:

*Number*.—45.

*Length*.—Approximately 0.7 cm.

*Style*.—Length: About 0.5 cm. Color: Near RHS Red 47B.

*Stigma*.—Shape: clustered. Color: Near RHS Yellow-Orange 18B.

Receptacle:

*Height*.—15 mm.

*Diameter*.—7 mm.

*Shape*.—Obovate.

*Texture*.—Glabrous.

*Color*.—Near RHS Green 144A.

OTHER CHARACTERISTICS

Seeds and fruits: No fruit and seed set observed to date.

Disease/pest resistance: Excellent disease resistance; resists powdery mildew/black spot pathogens. Neither resistant nor susceptible to typical pests of garden roses.

Temperature tolerance: Approximate range −31° C. to 38° C.

What is claimed is:

1. A new and distinct cultivar of *Rosa* hybrid plant named 'ChewPatout' as herein illustrated and described.

* * * * *